(12) United States Patent
Adachi et al.

(10) Patent No.: US 8,765,929 B2
(45) Date of Patent: Jul. 1, 2014

(54) PROMOTER FOR USE IN TRANSFORMATION OF ALGAE

(75) Inventors: Masao Adachi, Kochi (JP); Keizo Nagasaki, Hatsukaichi (JP); Yuji Tomaru, Hatsukaichi (JP)

(73) Assignee: Kochi University, Kochi (JP)

( * ) Notice: Subject to any disclaimer, the term of this patent is extended or adjusted under 35 U.S.C. 154(b) by 253 days.

(21) Appl. No.: 13/145,858

(22) PCT Filed: Jan. 22, 2010

(86) PCT No.: PCT/JP2010/050843
§ 371 (c)(1),
(2), (4) Date: Jul. 22, 2011

(87) PCT Pub. No.: WO2010/084969
PCT Pub. Date: Jul. 29, 2010

(65) Prior Publication Data
US 2011/0300633 A1  Dec. 8, 2011

(30) Foreign Application Priority Data

Jan. 23, 2009 (JP) ................. 2009-013577

(51) Int. Cl.
C12N 15/63 (2006.01)
C12N 15/82 (2006.01)
A01H 1/00 (2006.01)

(52) U.S. Cl.
USPC ........ 536/24.1; 800/287; 800/278; 435/320.1

(58) Field of Classification Search
USPC ....................................................... 536/24.1
See application file for complete search history.

(56) References Cited

U.S. PATENT DOCUMENTS 6,027,900 A * 2/2000 Allnutt et al. ................ 435/6.15

OTHER PUBLICATIONS

Fourgoux-Nicol et al. 1999, Plant Molecular Biology 40:857-872.*
Chinese Office Action issued Jul. 4, 2012 in corresponding Chinese Application No. 201080005172.8 (with English translation).
Supplementary European Search Report dated Aug. 3, 2012 in EP Application No. 10733576.2.
Dunahay T et al., "Genetic Transformation of the Diatoms *Cyclotella cryptica* and *Navicula saprophila*", Journal of Phycology, vol. 31, 1995, pp. 1004-1012.
Sakaue K et al., "Development of gene expression system in a marine diatom using viral promoters of a wide variety of origin", Physiologia Plantarum, vol. 133, 2008, pp. 59-67.
ten Lohuis MR et al., "Genetic transformation of dinoflagellates (Amphidinium and Symbiodinium): expression of GUS in microalgae using heterologous promoter constructs", The Plant Journal, vol. 13, 1998, pp. 427-435.
Walker T et al., "Algal Transgenics in the Genomic Era", Journal of Phycology, vol. 41, 2005, pp. 1077-1093.
Tomaru Y et al., "Isolation and characterization of a new single-stranded DNA virus infecting the cosmopolitan marine diatom *Chaetoceros debilis*", Aquatic Microbial Ecology, vol. 50, 2008, pp. 103-112.
Drocourt D et al., "Cassettes of the *Streptoalloteichus hindustanus* ble gene for transformation of lower and higher eukaryotes to phleomycin resistance", Nucleic Acids Research, vol. 18, 1990, p. 4009.
Poulsen N et al., "A new molecular tool for transgenic diatoms: Control of mRNA and protein biosynthesis by an inducible promoter-terminator cassetee", FEBS Journal, 2005, pp. 3413-3423.
Poulsen N et al., "Molecular Genetic Manipulation of the Diatom *Thalassiosira pseudonana* (Bacillariophyceae)", Journal of Phycology, vol. 42, 2006, pp. 1059-1065.
Javahery R et al., "DNA Sequence Requirements for Transcriptional Initiator Activity in Mammalian Cells", Molecular and Cellular Biology, vol. 14, 1994, pp. 116-127.
McLeod A et al., "Core Promoter Structure in the Oomycete *Phytophthora infestans*", Eukaryotic Cell, vol. 3, 2004, pp. 91-99.
Purnell BA et al., "TFIID sequence recognition of the initiator and sequences farther downstream in *Drosophila* class II genes", Genes and Development, vol. 8, 1994, pp. 830-842.
Liston DR et al., "Analysis of a Ubiquitous Promoter Element in a Primitive Eukaryote: Early Evolution of the Initiator Element", Molecular and Cellular Biology, vol. 19, 1999, pp. 2380-2388.
Yoshida T et al., "Cyanophage Ma-LMM01 no Tensha Chosetsu Ryoiki to sono Kansen Katei ni Okeru Idenshi Tensha Kaiseki", The Japanese Society of Virology Gakujutsu Shukai Program Shorokushu, vol. 55, 2007, p. 415.
Kang M et al., "The regulation activity of *Chlorella* virus gene 5' upstream sequence in *Escherichia coli* and eucaryotic algae", Sheng Wu Gong Cheng Xue Bao, vol. 16, 2000, pp. 443-446.
Mitra A et al., "A *Chlorella* Virus Gene Promoter Functions as a Strong Promoter Both in Plants and Bacteria", Biochemical and Biophysical Communications, vol. 204, 1994, pp. 187-194.
Jung HK et al., "Activity of Early Gene Promoters from a Korean *Chlorella* Virus Isolate in Transformed *Chlorella* Algae", Journal of Microbiology and Biotechnology, vol. 16, 2006, pp. 952-960.
Miyakawa A et al., "Sorui Kansensei Virus Promoter o Mochiita Kaisan Keiso no Keishitsu Tenkankei no Kaihatsu", Japanese Society of Marine Biotechnology Taikai Koen Yoshishu, vol. 12, 2009, p. 104.
Ikeya T et al., Kaiyo Monthly, 2000, p. 10.
Chinese Office Action issued Feb. 25, 2013 in Application No. 201080005172.8 along with its English translation.
Office Action issued Feb. 17, 2014 in corresponding European Application No. 10 733 576.2.

* cited by examiner

*Primary Examiner* — Li Zheng
(74) *Attorney, Agent, or Firm* — Wenderoth, Lind & Ponack, L.L.P.

(57) ABSTRACT

The objective of the present invention is to provide a transformation method that is applicable to a wide variety of species of algae with high efficiency. The promoter of the present invention is characterized in containing a polynucleotide constituting a non-coding region located upstream from a gene encoding a replication-associated protein of a CdebDNA virus or the like.

4 Claims, 7 Drawing Sheets

(2)

(1)

SEQUENCE LISTING

```
<160> NUMBER OF SEQ ID NOS: 9

<210> SEQ ID NO 1
<211> LENGTH: 480
<212> TYPE: DNA
<213> ORGANISM: CdebDNA Virus

<400> SEQUENCE: 1
ggacccatac cccgagagcc gtgcatcgcc gggggcgatg cactccgaca aattataaaa      60
atgttcgctt cggcaggggc cccggcggtc cagtgacggt attctccccc tcattaggtt     120
gctagagcac taatgcctcc ggcgggcaaa cttattgcag ctcggagagc ggcacgagtt     180
ggctaaatgc ctgcggcgct cattgatagt cttgatcata agactaattg cagctcggat     240
acgtgcacga gttggctaaa tgcctgcggc gcgcaataaa taatgcacga acgcattaac     300
gcgcggtgtt ctcatcacgc gccgttcttt tctggcgcgg gttcgggtta gggttctggt     360
tctgcatgcc ataccgagta tttctacgta gagtctacag acccaaaact agatgtgggc     420
agagttctgg gtcgattgtt cataaatatc cacaatcgtt tcatatttta caataaaatg     480

<210> SEQ ID NO 2
<211> LENGTH: 46
<212> TYPE: DNA
<213> ORGANISM: Artificial Sequence
<220> FEATURE:
<223> OTHER INFORMATION: Synthetic construct

<400> SEQUENCE: 2
ggggacaagt ttgtacaaaa aagcaggctg cggacccata ccccga                     46

<210> SEQ ID NO 3
<211> LENGTH: 54
<212> TYPE: DNA
<213> ORGANISM: Artificial Sequence
<220> FEATURE:
<223> OTHER INFORMATION: Synthetic construct

<400> SEQUENCE: 3
ggggacaact tgtatagaa aagttgggtt ttattgtaaa atatgaaacg attg             54

<210> SEQ ID NO 4
<211> LENGTH: 17
<212> TYPE: DNA
<213> ORGANISM: Artificial Sequence
<220> FEATURE:
<223> OTHER INFORMATION: Synthetic construct

<400> SEQUENCE: 4
gtaaaacgac ggccagt                                                     17
```

```
<210> SEQ ID NO 5
<211> LENGTH: 40
<212> TYPE: DNA
<213> ORGANISM: CdebDNA Virus

<400> SEQUENCE: 5
acgcgcggtg ttctcatcac gcgccgttct tttctggcgc                              40

<210> SEQ ID NO 6
<211> LENGTH: 49
<212> TYPE: DNA
<213> ORGANISM: Artificial Sequence
<220> FEATURE:
<223> OTHER INFORMATION: Synthetic construct

<400> SEQUENCE: 6
ggggacaagt ttgtacaaaa aagcaggctt aacgcgcggt gttctcatc                    49

<210> SEQ ID NO 7
<211> LENGTH: 49
<212> TYPE: DNA
<213> ORGANISM: Artificial Sequence
<220> FEATURE:
<223> OTHER INFORMATION: Synthetic construct

<400> SEQUENCE: 7
ggggacaagt ttgtacaaaa aagcaggctt agggttcggg ttagggttc                    49

<210> SEQ ID NO 8
<211> LENGTH: 49
<212> TYPE: DNA
<213> ORGANISM: Artificial Sequence
<220> FEATURE:
<223> OTHER INFORMATION: Synthetic construct

<400> SEQUENCE: 8
ggggacaagt ttgtacaaaa aagcaggctt accataccga gtatttcta                    49

<210> SEQ ID NO 9
<211> LENGTH: 49
<212> TYPE: DNA
<213> ORGANISM: Artificial Sequence
<220> FEATURE:
<223> OTHER INFORMATION: Synthetic construct

<400> SEQUENCE: 9
ggggacaagt ttgtacaaaa aagcaggctt acaaaactag atgtgggca                    49
```

PROMOTER FOR USE IN TRANSFORMATION OF ALGAE

This application is a U.S. national stage of International Application No. PCT/JP2010/050843 filed Jan. 22, 2010.

TECHNICAL FIELD

The present invention relates to a novel promoter used for transforming algae, a vector containing the promoter, and a method for transforming algae using the vector.

BACKGROUND ART

It is very important to utilize sunlight which is a permanent and stable energy source in considering an energy countermeasure. Photosynthesis by plants is an excellent system capable of transforming sunlight energy to chemical energy most efficiently, and absorbs and assimilates carbon dioxide and excess nutrient salts in the environment. In addition, oxygen is emitted. The development of a technique utilizing plants is therefore expected as a solution for the energy problems.

Among plants, algae live in both of seawater and freshwater that abundantly exist, and are huge in amount. In addition, algae have a significant photosynthesis ability. Further, some of algae produce a useful compound such as unsaturated fatty acid and anti-tumor compound. Furthermore, since some of diatoms produce a useful inorganic substance, a technique called as biomineralization by diatoms is focused. As described above, algae can be said to be important organisms as useful resources.

When an organism is utilized industrially, a transformation technique for introducing a useful gene is generally used. The transformation technique is also used for knocking out a specific gene or preventing the action thereof in order to elucidate the function of the gene.

The transformation of algae, especially diatoms and green algae, has been conventionally carried out. In such a conventional method, an endogenous promoter is separated, a gene is conjugated with the promoter, and the promoter is introduced into algae. However, this method is far from efficient, since a lot of effort and time is required, for separating an endogenous promoter. There is also a problem that the transformation efficiency of algae, particularly of marine algae, is originally very low.

On the other hand, in transformation of animals or plants other than algae, a promoter derived from a virus rather than an endogenous promoter is generally used. For example, a CaMV35S promoter separated from a cauliflower mosaic virus (CaMV) infecting cruciferous plants is used for transforming a wide range of plants without limited to cruciferous plants. For transformation of an animal cell, a CMV promoter separated from a cytomegalovirus (CMV) and a SV40 promoter separated from a simian virus 40 (SV40) are widely used.

Unlike the above situation, in transformation of algae, there is known little example in which an exogenous virus promoter is used.

For example, Non-patent document 1 discloses an experimental example of transforming a diatom *Cycrotela cryptica* by using a CaMV35S promoter; however, it is reported that a transformant could not be obtained.

Non-patent document 2 discloses that a GUS gene is introduced into a diatom *Phaeodactylum tricornutum* by using a CMV promoter, a CaMV35S promoter or a Rous sarcoma virus (RSV) promoter; as a result, GUS (β-glucuronidase) was expressed in any cases.

Non-patent document 3 discloses that when a GUS gene is introduced into dinoflagellates *Amphidinium* or *Symbiodinium* by using a CaMV35S promoter, GUS was expressed. However, according to another document (Non-patent document 4), there is no report describing that another group succeeds in transformation of dinoflagellates in spite of diligent efforts.

PRIOR ART

Non-Patent Document

Non-patent document 1: Dunahay T. G. et al., Journal of Phycology, vol. 31, pp. 1004-1012 (1995)
Non-patent document 2: Sakaue K. et al., Physiologia plantarum, vol. 133, pp. 59-67 (2008)
Non-patent document 3: Lohuis M. R. et al., The Plant Journal, vol. 13, pp. 427-435 (1998)
Non-patent document 4: Walker T. L. et al., Journal of Phycology, vol. 41, pp. 1077-1093 (2005)

DISCLOSURE OF THE INVENTION

Problems to be Solved by the Invention

As described above, there are examples reporting success in transforming algae by using a viral promoter such as a CaMV35S promoter derived from a cauliflower mosaic virus, although the number of examples is very small.

However, there is also a report that transformant was not obtained or reproducibility was not achieved. According to the findings of the present inventors, a CaMV35S promoter that is generally used in transformation of other plants has a very small application range for algae. It is desired that a promoter used for transformation is applicable to a wide variety of species of algae, since algae exist abundantly and include various species having potential usefulness. Further, in general, since the transformation efficiency of algae, particularly marine algae, is very low, development of a transformation technique with high efficiency is much-needed.

Under the above-mentioned situation, the problem to be solved by the present invention is to provide a transformation method that is applicable to a wide variety of species of algae with high efficiency.

Means for Solving the Problems

The present inventors conducted intensive studies to solve the above-mentioned problem. As a result, the inventors found that a promoter located upstream from a gene considered as encoding replication-associated protein of a *Chaetoceros debilis* DNA virus (CdebDNAV) is able to transform several species which belongs to not only a centric diatom but also pennate diatoms, and accomplished the present invention.

The novel promoter according to the present invention is characterized in containing any one of the following polynucleotide (1) to (3):

(1) a polynucleotide constituting a non-coding region located upstream from a gene encoding a replication-associated protein of a CdebDNA virus;
(2) a polynucleotide corresponding to the polynucleotide (1) with one or more nucleotide deletions, substitutions or additions and activating expression of a gene encoding an arbitrary protein in an algal cell;

(3) a polynucleotide hybridizing with the polynucleotide (1) in a stringent condition and activating expression of a gene encoding an arbitrary protein in an algal cell.

The vector according to the present invention is characterized in comprising the above promoter and a gene encoding an arbitrary protein. The method for transforming an algal according to the present invention is characterized in comprising the steps of producing the above-described vector, and introducing the vector into the algal cell.

MODE FOR CARRYING OUT THE INVENTION

Figure 1:
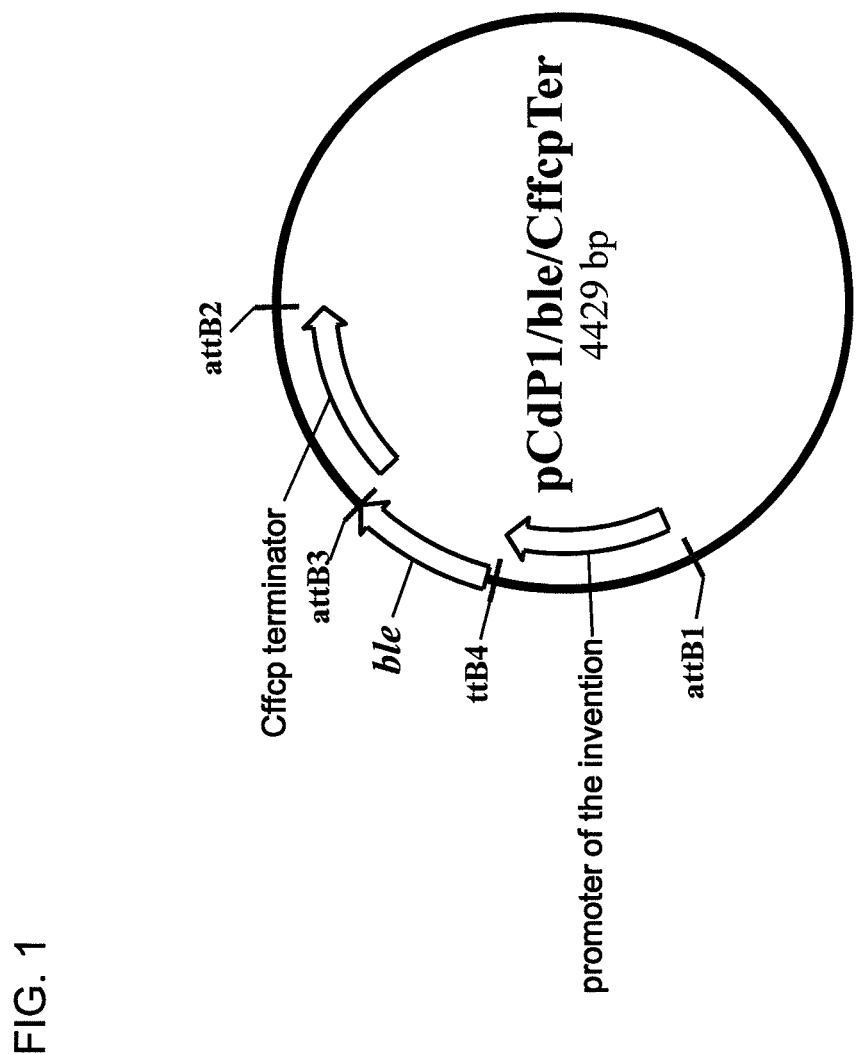
FIG. 1 is a view showing one example of a structure of a plasmid vector containing a promoter according to the present invention.

The first promoter according to the present invention has (1) a polynucleotide constituting a non-coding region located upstream from a gene encoding a replication-associated protein of a CdebDNA virus.

A CdebDNA virus infects a diatom *Chaetoceros debilis*. There are conventionally few examples reporting a virus representing infectiousness on algae, particularly on marine algae; however, the present inventors succeeded in separating a variety of viruses from algae such as raphidophyceae, dinoflagellates and diatoms in recent years. The CdebDNA virus according to the present invention is one of the marine algae infectious viruses separated by the present inventors.

The gene encoding a replication-associated protein is not particularly limited as far as the gene is involved in the replication of a CdebDNA virus and actively expressed.

In the present invention, a coding region refers to a part that is translated into a protein through mRNA, and a non-coding region refers to a part other than the coding region. In other words, a non-coding region refers to a part located upstream from a start codon such as ATG, and includes not only a part that is not transcribed into mRNA but also a part that is not translated into a protein although it is transcribed into mRNA.

In general, a promoter has a core element that holds the key of transcription, and a regulatory element that promotes or prevents transcription. When a gene is introduced, it is particularly important to utilize a core element. As such a core element, a TATA box, an initiator element (Inr), a downstream element and the like are known, and as a regulatory element, a CAAT box, a GATA box and the like are known. The present inventors examined a nucleotide sequence in the region upstream from a gene encoding a replication-associated protein of a CdebDNA virus; as a result, found 5'-CAAT-3' as a CAAT box I, 5'-WGATAR-3' (wherein W represents A or T, and R represents A or G) as a GATA box, and 5'-YYA$_{+1}$N(A/T)YY-3' (wherein Y represents C or T) as an initiator element (Inr), however, a TATA box, which is found in a promoter of eukaryote and the like, was not found. It is therefore supposed that the Inr found in the sequence upstream from the above gene functions as a core element both in pennate diatoms and centric diatoms, and enables transformation. On the other hand, when a pennate diatom endogenous promoter (CffcpA-1A) containing Inr which is very similar to the above Inr is used, it is impossible to transform centric diatoms. In conclusion, it can be said that the high transformability exerted by the polynucleotide (1) according to the present invention does not result from at least the TATA box and the initiator element, and there is high possibility that an entirely different unknown sequence functions as a core element.

As the polynucleotide (1), those having polynucleotide sequences of SEQ ID NO: 1 and SEQ ID NO: 5 can be exemplified. The sequence of SEQ ID NO: 5 corresponds to a sequence having about 40 bases from about 30 bases upstream from Inr in the upstream sequence of the gene encoding a replication-associated protein of a CdebDNA virus, and there is no a CAAT box nor a GATA box as well as Inr in the sequence.

A second promoter according to the present invention is (2) a polynucleotide corresponding to the polynucleotide (1) with one or more nucleotide deletions, substitutions or additions and activating expression of a gene encoding an arbitrary protein in an algal cell.

In the polynucleotide (2), the number of nucleotides that are deleted, substituted or added is preferably not less than 1 and not more than 200, more preferably not less than 1 and not more than 100, further preferably not less than 1 and not more than 70, further preferably not less than 1 and not more than 30, further preferably not less than 1 and not more than 20, further preferably not less than 1 and not more than 10, and particularly preferably not less than 1 and not more than 5.

A third promoter of the present invention is (3) a polynucleotide hybridizing with the polynucleotide (1) in a stringent condition and activating expression of a gene encoding an arbitrary protein in an algal cell.

In terms of the polynucleotide (3), the stringent condition refers to causing hybridization at 65° C. in 2×SSC containing 0.1% SDS, followed by washing twice with 0.1×SSC-0.1% SDS.

In terms of the polynucleotides (2) and (3), the polynucleotide that activates expression of a gene encoding an arbitrary protein in an algal cell refers to a polynucleotide capable of allowing expression of a gene which encodes an arbitrary protein and is conjugated downstream from the polynucleotide, when the polynucleotide is introduced into an algal cell.

As to the polynucleotides (2) and (3), the homology with the polynucleotide (1) is preferably not less than 50%, more preferably not less than 70%, further preferably not less than 80%, further preferably not less than 90%, further preferably not less than 95%, further preferably not less than 98%, and particularly preferably not less than 99%.

The polynucleotides (1) to (3) can be separated from the upstream sequence of a gene encoding a replication-associated protein of a CdebDNA virus or a mutant thereof. However, the polynucleotides may be chemically synthesized. The polynucleotides (1) to (3) can be amplified from a template by PCR, to be used.

The vector according to the present invention includes the above promoter and a gene encoding an arbitrary protein.

The kind of the vector is not particularly limited as far as the vector can be introduced into an algal cell, and any of a plasmid vector and a virus vector may be used. Since it is hard to be said that researches of virus that infect algae, particularly marine algae, are sufficiently advanced, a plasmid vector is preferably used.

In the present invention, the "arbitrary protein" is not particularly limited, and may be any useful proteins desired to be produced.

The vector according to the present invention may include other sequences that are included in a general vector. As such sequences, a selection marker gene for identifying algae into which the vector of the present invention is introduced, and a terminator functioning in an algal cell can be exemplified.

As a method for preparing the vector according to the present invention, ordinary methods may be used. For example, each sequence described above and a donor vector may be annealed after being digested with a restriction enzyme, and the annealed sequences may be bound using a DNA ligase. Alternatively, each sequence may be cloned into a vector by a simple known method utilizing a Clonase reaction.

The method for transforming an algal according to the present invention is characterized in comprising the steps of producing the above-described vector, and introducing the vector into the algal cell.

As a method for preparing the vector of the present invention, the methods known by a person skilled in the art may be used as described above.

As a method for introducing the vector of the present invention into an algal cell, known methods such as a particle gun method, a glass beads stirring method, a microinjection method, an agrobacterium method, a lithium acetate method, a calcium phosphate method and a protoplast method may be used. However, in the case of marine algae, an electroporation method is not appropriate since marine algae need to be grown in a media having high salt concentration.

The algal cell transformed with the vector of the present invention can be identified by being cultured in a selection medium suited for the introduced selection marker gene.

EXAMPLES

Hereinafter, the present invention is described in more detail by demonstrating Examples; however, the present invention is not limited by the Examples, and of course, may be practiced with appropriate modification within the range conforming to the above or below description, and any of the modifications are included within the technical scope of the present invention.

Example 1

Separation of a CdebDNA Virus Promoter According to the Present Invention (1) Extraction of Genomic DNA of a Virus Infecting Marine Algae According to the method described in Tomaru, Y. et al., Aquatic Microbial Ecology, vol. 50, pp. 103-112 (2008), a genome was extracted from a *Chaetoceros debilis* DNA virus (CdebDNAV) CdebDNAV18 strain living on a centric diatom *Chaetoceros debilis* as a host.

Specifically, first, algal cell and algal cell debris were removed by filtering a viral liquid (10 mL) through a 0.22 μm filter (manufactured by MILLIPORE, Millex-GS, pore size: 0.22 μm). To the obtained filtrate, 40% polyethyleneglycol 6000 solution (manufactured by Woko) was added to make the final concentration 10 w/v %. The mixture was left still overnight at 4° C. The mixture was then transferred into a centrifugal tube (manufactured by Nalgen, UltraBottle Assemblies), and centrifuged at 57,000×g, 4° C. for 1.5 hours using an ultracentrifuge (manufactured by BECKMAN, Ultracentrifuge L8-70M). Then, the supernatant was removed. Viral particles were washed by mixing the obtained precipitate with a phosphate buffer (10 mM sodium dihydrogen phosphate, 10 mM sodium hydrogen phosphate, pH 7.2, 5 mL). Again, after the mixture was centrifuged at 217,000×g, 4° C. for 4 hours and the supernatant was removed in a similar manner, the obtained precipitate was dissolved in sterilized purified water (manufactured by Millipore, milliQ (registered trademark), 300 μL). The solution was transferred into a 1.5 mL Eppendorf tube, and proteinase K and 10% sarcosyl were added to make the respective final concentrations 1 mg/mL and 1 w/v %. The mixture was incubated at 55° C. for 1.5 hours. Then, a phenol/chloroform treatment and a chloroform treatment were carried out with routine methods. To the obtained supernatant, a one-tenth amount of 3M sodium acetate (pH 4.8) was added, and further a 2.5 times amount of ethanol was added. The resultant solution was left still at −80° C. for 1 hour. Then, the solution was centrifuged at 14,000 rpm, 4° C. for 10 minutes using a high-speed micro centrifuge (manufactured by KUBOTA, KUBOTA3740), and the obtained precipitate was washed with 70% ethanol and then dried. The dried product was dissolved in sterilized milliQ water (20 μL) to obtain a DNA solution. Further, purification was carried out with a cetyl trimethyl ammonium bromide method (CTAB method) described in the aforementioned document (Tomaru, Y. et al. (2008)). First, to the above DNA solution, a TE buffer (10 mM Tris-HCl (pH8.0), 1 mM EDTA (pH8.0)) was added to make the total amount 200 μL. To the DNA solution, a CTAB solution (1.6 M NaCl, 0.1 M EDTA, 2 w/v % CTAB, 200 μL) was added, and the mixture was incubated at 65° C. for 1 hour. To the solution, chloroform (400 μL) was added. The mixture was shaken for 5 minutes, and then centrifuged at 14,000 rpm, 4° C. for 10 minutes using the high-speed micro centrifuge described above. To the resultant solution, a double amount of ethanol was added. The mixture was left still at −80° C. for 1 hour. Then, the mixture was centrifuged at 14,000 rpm, 4° C. for 10 minutes using the same high-speed micro centrifuge, and the obtained precipitate was washed with 70% ethanol and then dried. The precipitate was dissolved in sterilized milliQ water (300 μL), to prepare a DNA solution.

(2) Separation of CdebDNA Virus Promoter

Sequence information of the genomic DNA of a CdebDNA virus obtained in the above (1) was compared with a database using Blast (DDBJ), and ORF contained in the CdebDNA virus DNA was searched using ORF finder (NCBI), to detect a region encoding a protein considered to be involved in the replication of the virus. The region of from +107 to −370 upstream from the ATG sequence which seemed to be a translation starting point in this sequence was amplified by a PCR reaction with a CdP1L/attB1 primer (SEQ ID NO: 2) and a CdP1-2R/attB4 primer (SEQ ID NO: 3). The nucleotide sequence of from 5 to 31 in SEQ ID NO: 2 and the nucleotide sequence of from 5 to 29 in SEQ ID NO: 3 show attB sequences required for BP Clonase reaction for construction of a plasmid as described later. The obtained nucleotide sequence of the obtained CdebDNA virus promoter is shown in SEQ ID NO: 1. In SEQ ID NO: 1, "ATG" is a start codon, which is not contained in a promoter.

The conditions of the PCR reaction is shown below. As a PCR reaction mixture, 10× buffer (manufactured by TaKaRa, 5 µL), dNTP Mix (manufactured by TaKaRa, 4 µL), Ex Taq (manufactured by TaKaRa, 0.25 µL, 5 U/µL), genomic DNA of CdebDNA virus (1 µL) and two kinds of primers (10 pmol/µL, each 5 µL) were mixed, and lastly sterilized milliQ water was added to make the total volume 50 µL. Then, the cycle consisting of 10 seconds at 98.0° C., 30 seconds at 45.0° C. and 60 seconds at 72.0° C. was repeated 40 times, followed by a final reaction at 72.0° C. for 5 minutes.

For confirming amplification of a fragment, electrophoresis was conducted. For the electrophoresis, a TAE buffer (Tris acetate buffer) and agarose S (manufactured by NIPPON GENE Co., Ltd.) 1.5% gel were used. A sample for electrophoresis was prepared by adding 1 µL of 10× loading buffer (manufactured by TaKaRa) to each 9 µL of the PCR product to be mixed. As a DNA molecular weight marker, 100 bp ladder (manufactured by TOYOBO, Code No. DNA-030X, 2 µL) was used and electrophoresed concurrently. Electrophoresis was carried out in a condition of 100 V for about 30 minutes using a Mupid electrophoresis tank (manufactured by ADVANCE Co., Ltd.). After end of the electrophoresis, staining with ethidium bromide was conducted by a routine method (Sambrook and Russell, 2001) and the gel was photographed under ultraviolet irradiation.

Example 2

Preparation of Vector Containing CdebDNA Virus Promoter According to the Present Invention (1) Preparation of Each Entry Clone Plasmid An entry clone plasmid vector into which the CdebDNA virus promoter obtained in Example 1, a Zeocin resistance gene (ble) (Drocourt, D. et al., Nucleic Acids Research, 18, p. 4009 (1990)) as a transgene and a fcp terminator of *Cylindrotheca fusiformis* (Poulsen, N. et al., FEES Journal, 272, pp. 3413-3423 (2005)) were introduced was prepared using a Multisite Gateway (registered trademark) Pro Kit (manufactured by Invitrogen).

Specifically, a solution of the CdebDNA virus promoter obtained in Example 1 having an attB sequence required for the Clonase reaction for construction of a plasmid was purified using a 30% PEG8000/30 mM magnesium chloride solution (manufactured by Invitrogen). More specifically, to the CdebDNA virus promoter solution (25 µL), sterilized milliQ water (75 µL) was added to make a solution of 100 µL. To the solution, the 30% PEG8000/30 mM magnesium chloride solution (50 µL) was added to be mixed, and the mixture was centrifuged at 14,000 rpm for 15 minutes using a high-speed microcentrifuge (manufactured by KUBOTA, KUBOTA 3740). Then, the supernatant was removed, and the obtained precipitate was dissolved in sterilized milliQ water (10 µL). Next, the solution (50 fmoles) and a donor vector (manufactured by Invitrogen, pDONR221 P1-P4, 100 ng/µL) were mixed, and the solution was added with sterilized milliQ water to make a total of 8 µL mixture. The donor vector had an attP sequence required for a Clonase reaction for construction of a plasmid. To the mixture, BP Clonase (trade name) II Enzyme Mix (manufactured by Invitrogen, 2 µL) was further added to be mixed, and the mixture was allowed to react at 25° C. for 1 hour. To the reaction mixture, proteinase K (manufactured by Invitrogen, 1 µL) was then added. The mixture was treated at 37° C. for 10 minutes. The reaction mixture (2.5 µL) was mixed with One Shot (registered trademark) Mach1 (registered trademark) T1$^R$ chemically competent cells (manufactured by Invitrogen, 25 µL), and the mixture was left still on ice for 30 minutes. Then, a heat shock treatment was carried out at 42° C. for 30 seconds, and the mixture was immediately transferred onto the ice and left still for 2 minutes. Then, SOC (manufactured by Invitrogen, 250 mL) was added, and culture was carried out under shaking at 37° C. for 1.5 hours. The cultured bacterial mixture (275 µL) was spread on a LB agar medium (1% triptone, 0.5% yeast extract, 1% NaCl, 1.5% agar) containing 50 µg/mL kanamycin. The medium was cultured upside down in a multi shaker oven (manufactured by TIETECH) at 37° C. overnight (about 10 hours). The obtained colonies were inoculated to a LB liquid medium (10 mL) using a platinum loop, and cultured under shaking at 37° C. overnight. From the culture liquid (3 mL), an entry clone plasmid in which the CdebDNA virus promoter having an attP sequence required for Clonase reaction was extracted using Pure Yield Plasmid Miniprep System (manufactured by Promega).

Also, a Zeocin-resistance gene (ble) having an attB sequence required for BP Clonase reaction for construction of a plasmid was amplified in a similar manner to Example 1, and introduced into pDONR221 P4r-P3r which was a donor vector having an attP sequence required for BP Clonase reaction in a similar manner as described above, to obtain an entry clone plasmid in which an antibiotic resistance gene having an attL sequence required for LR Clonase reaction was introduced.

Further, a fcp terminator of *Cylindrotheca fusiformis* having an attB sequence required for BP Clonase reaction for construction of a plasmid was amplified in a similar manner to Example 1, and introduced into pDONR221 P3-P2 which was a donor vector having an attP sequence required for BP Clonase reaction in a similar manner as described above, to obtain an entry clone plasmid into which a terminator having an attL sequence required for LR Clonase reaction was introduced.

(2) Preparation of Destination Plasmid

A destination plasmid was prepared by incorporating a Reading Frame Casette having an attR sequence required for LR Clonase reaction into a pBluescript SK—(manufactured by Stratagene) using Gateway (registered trademark) Vector Conversion System with One Shot (registered trademark) ccdB Survival (registered trademark) Competent Cells (manufactured by Invitrogen).

First, the pBluescript SK—(2 µg) was digested at 37° C. for 3 hours using 20 U of a restriction enzyme EcoRI (manufactured by TOYOBO, 10 U/µL). DNA was precipitated by adding ethanol to the reaction mixture according to a routine method, to be collected. Next, the DNA was blunted by using a T4 DNA polymerase. Specifically, to the collected DNA, 10× buffer (5 µL), 2.5 mM dNTP (manufactured by TAKARA, 2 µL), T4 DNA polymerase (manufactured by TOYOBO, 0.5 U/µL, 1 µL) and sterilized milliQ water (42 µL) were added, to prepare a total of 50 µL of reaction mixture. The reaction mixture was incubated at 12° C. for 15 minutes. To the reaction mixture, sterilized milliQ water (350 µL) was immediately added. The mixture was subjected to a phenol/chloroform treatment and a chloroform treatment according to routine methods, followed by ethanol precipitation to collect DNA. Next, for preventing recircularization of the plasmid digested with the restriction enzyme, the fragments were subjected to a 5'-end dephosphorylation treatment using CIAP (manufactured by TaKaRa, Calf intestine Alkaline Phosphatase). To the DNA having subjected to the blunting treatment, 10×CIAP buffer (5 μL) and CIAP (0.1 U/μL, 1 μL) were added, and sterilized milliQ water was added to prepare a total of 50 μL of reaction mixture. The reaction mixture was incubated at 37° C. for 15 minutes, and sequentially at 56° C. for 15 minutes, and CIAP (0.1 U/μL, 1 μL) was added thereto again and the mixture was incubated at 37° C. for 15 minutes and sequentially at 56° C. for 15 minutes. To the reaction mixture, a 10% SDS solution (2.5 μL), a 500 mM EDTA solution (0.5 μL) and a proteinase K solution (20 mg/μL, 0.5 μL) were further added, and the mixture was incubated at 56° C. for 30 minutes and sequentially at 75° C. for 10 minutes. Thereafter, a phenol/chloroform treatment and a chloroform treatment were carried out according to routine methods. Next, DNA was collected by ethanol precipitation, and dissolved in sterilized milliQ water (10 μL).

The obtained pBluescript SK—having blunt ends was mixed with a Reading Frame. Casette A (manufactured by Invitrogen, RfA) for conjugation by using a T4 DNA ligase associated with pGEM-T Vector Systems Kit (manufactured by Promega). First, into a 0.2 mL PCR tube sterilized in an autoclave, 2× rapid ligation buffer (manufactured by Promega, 5 μL), pBluescript SK— (100 ng/μL, 0.5 μL), RfA (5 ng/μL, 2 μL), T4 DNA ligase (manufactured by Promega, 3 U/μL, 1 μL) and sterilized milliQ water (1.5 μL) were added, to prepare a total of 10 μL of reaction mixture. The reaction mixture was stored at room temperature for 1 hour, and incubated at 4° C. overnight (16 hours or more). This ligation solution (5 μL) was mixed with ccdB Survival Competent Cells (manufactured by Invitrogen, 50 μL), and the mixture was left still for 30 minutes on ice. Then, the mixture was subjected to a heat shock treatment at 42° C. for 30 seconds, immediately transferred onto ice, and left still for 2 minutes. Next, SOC (250 mL) was added thereto and the mixture was cultured under shaking at 37° C. for 1.5 hours. The cultured bacteria mixture (300 μL) was spread on a LB agar medium containing 25 μg/mL chloramphenicol and 50 μg/mL ampicillin. The medium was cultured upside down overnight in a multi shaker oven at 37° C.

The obtained colonies were inoculated to a LB medium (10 mL) using a platinum loop, and cultured under shaking overnight at 37° C. From the culture liquid (3 mL), a destination plasmid was extracted by using Pure Yield Plasmid Miniprep System (manufactured by Promega).

(3) Preparation of Expression Clone Plasmid Vector

An expression clone plasmid vector in which a promoter, an antibiotic resistance gene and a terminator were conjugated was prepared, by conducting LR Clonase reaction between the entry clone plasmid obtained in Example 2(1) and the destination plasmid obtained in Example 2(2) using Multisite Gateway Pro Kit (manufactured by Invitrogen).

Specifically, three kinds of entry clone plasmids (each 10 fmoles) each having a promoter, an antibiotic resistance gene and a terminator incorporated therein were mixed with a destination vector (20 fmoles), and sterilized milliQ water was further added thereto to prepare a total of 8 μL of a mixture. To the mixture, LR Clonase II PLUS Enzyme Mix (manufactured by Invitrogen, 2 μL) was added to be mixed, and the mixture was allowed to react at 25° C. for 16 hours. Thereafter, proteinase K (manufactured by Invitrogen, 1 μl) was added to the reaction mixture and the mixture was treated at 37° C. for 10 minutes. The reaction mixture (2.5 μL) was mixed with One Shot (registered trademark) Mach1 (registered trademark) T1$^R$ chemically competent cells (manufactured by Invitrogen, 25 μl), and the mixture was left still on ice for 30 minutes. Then, the mixture was subjected to a heat shock treatment at 42° C. for 30 seconds, immediately transferred onto ice, and left still for 2 minutes. Next, SOC (250 mL) was added to the mixture and culture was carried out under shaking at 37° C. for 1.5 hours. The cultured bacteria mixture (275 μL) was spread on a LB agar medium containing 50 μg/mL ampicillin. The medium was cultured upside down overnight in a multi shaker oven at 37° C. The obtained colonies were inoculated to a LB medium (10 mL) using a platinum loop, and cultured under shaking overnight at 37° C. From the culture mixture (3 mL), an expression clone plasmid vector was extracted by using Pure Yield Plasmid Miniprep System (manufactured by Promega).

(4) Confirmation of DNA Sequence

For confirming that an intended expression clone plasmid vector was prepared, a nucleotide sequence was determined by using a Dideoxy method.

A cycle sequencing PCR was carried out by using the expression clone plasmid vector (200 ng) prepared in Example 2(3) as a template. The reaction condition is shown below. The reaction mixture (10 μL) was composed of a template DNA (100 ng/μL, 2 μL), Big Dye Terminator Cycle Sequencing ver. 3.1 (manufactured by Applied Biosystems, 0.5 μL), 5× sequencing buffer (2 μL), primer (1.6 pmol/μL, 0.66 μL) and sterilized distilled water (4.84 μL). As the primer, M13M3 primer (SEQ ID NO: 4) was used. As a reaction condition, after heating at 95° C. for 5 minutes, a cycle of 10 seconds at 96° C., 5 seconds at 50° C. and 4 minutes at 60° C. was conducted 40 times. After the reaction, the reaction mixture was transferred to a 1.5 mL Eppendorf tube, and 3M sodium acetate (1 μL), 99.5% ethanol (25 μL) and 125 mM EDTA solution (1 μL) were added thereto, and the Eppendorf tube was flipped for mixing the mixture well, and then the mixture was left still for 15 minutes at room temperature. After centrifugation at 14,000 rpm, 4° C. for 20 minutes, the supernatant was removed carefully using a yellow tip, and 70% ethanol (35 μL) was added thereto to be mixed well. Again, after centrifugation at 14,000 rpm, 4° C. for 10 minutes, the supernatant was completely removed using a yellow tip, and the precipitate was left still at room temperature for 10 minutes with the lid open for drying.

To the dried pellet, formamide (manufactured by Applied Biosystems, 10 μL) was added, and the mixture was analyzed by using an ABI PRISM (registered trademark) 3100-Avant Genetic Analyzer (manufactured by Applied Biosystems) in a gene experiment facility, General Research Center, Kochi University. The nucleotide sequence of an expression clone plasmid vector was prepared by preliminarily incorporating nucleotide sequences of a promoter, an antibiotic resistance gene and a terminator into a nucleotide sequence of a destination plasmid using gene analysis software Vector NTI Advance Ver 10.0 (manufactured by Invitrogen). Next, the nucleotide sequence of the expression clone plasmid vector prepared on the computer was compared with a nucleotide sequence of an expression clone plasmid vector experimentally determined according to the above method by alignment using AlignX of Vector NTI Advance Ver 10.0, to confirm that the intended gene was introduced into the expression clone plasmid vector prepared in Example 2(3).

The structure of the obtained expression clone plasmid vector is shown in FIG. 1.

Example 3

Preparation of Vector Containing CdebDNA Virus Promoter According to the Present Invention A vector containing a CdebDNA virus promoter was prepared in a similar manner to Example 2 by using a nourseothricin resistance gene (nat) (Krugel et al., 1993) as an antibiotic resistance gene and a fcp terminator derived from *Thalassiosira pseudonana* (Poulsen, N. et al., Journal of Phycology, 42, pp. 1059-1065 (2006)) as a terminator.

Figure 2:
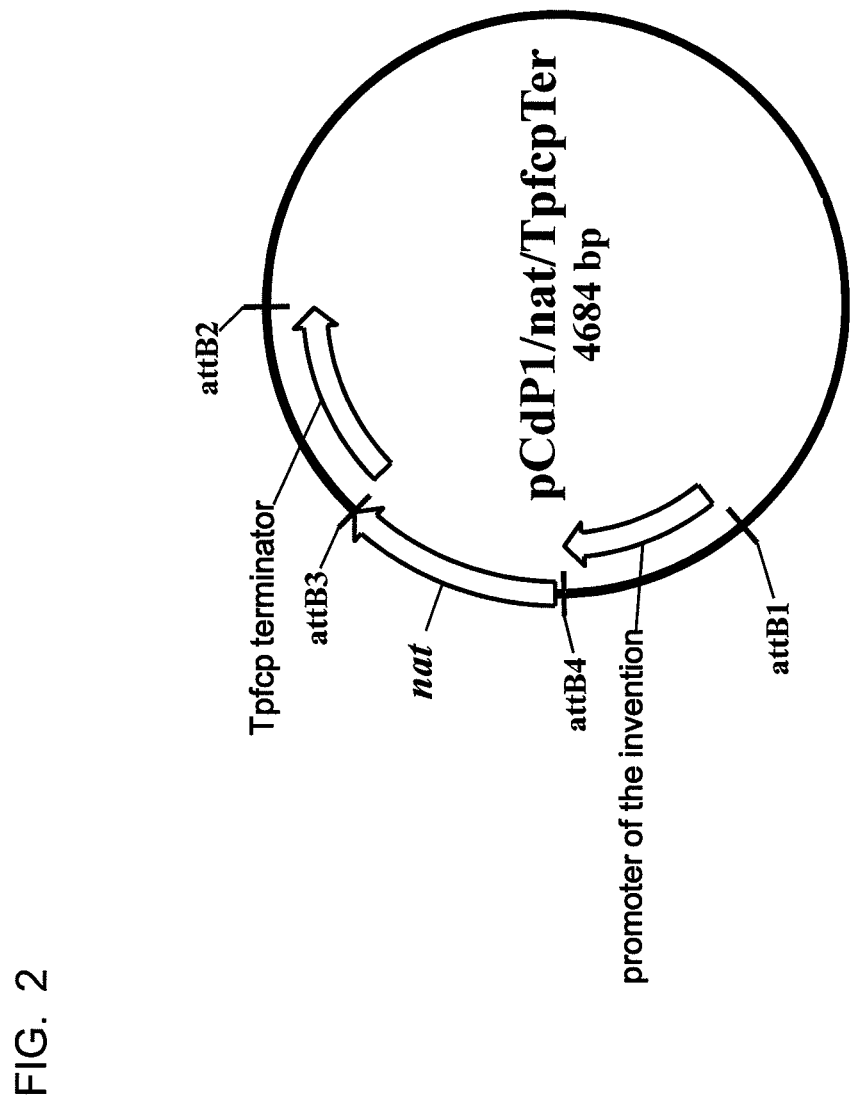
FIG. 2 is a view showing one example of a structure of a plasmid vector containing a promoter according to the present invention.

The structure of the obtained expression clone plasmid vector is shown in FIG. 2.

Comparative Examples 1 to 4

Preparation of a Vector Containing a Conventional Virus Promoter

In a similar manner to Example 2, a plasmid vector which had an endogenous promoter of pennate diatoms and into which a Zeocin resistance gene (ble) as an antibiotic resistance gene and a fcp terminator of *Cylindrotheca fusiformis* as a terminator were introduced (Comparative example 1), and a plasmid vector which had an endogenous promoter of centric diatoms and into which a nourseothricin resistance gene (nat) as an antibiotic resistance gene and a fcp terminator derived from *Thalassiosira pseudonana* as a terminator (Comparative example 2) were introduced were prepared.

In a similar manner to Example 2, a plasmid vector which had a promoter derived from a cauliflower mosaic virus (CaMV promoter) and into which a Zeocin resistance gene (ble) as an antibiotic resistance gene and a fcp terminator of *Cylindrotheca fusiformis* as a terminator were introduced (Comparative example 3), and a plasmid vector into which a nourseothricin resistance gene (nat) as an antibiotic resistance gene and a fcp terminator derived from *Thalassiosira pseudonana* as a terminator were introduced (Comparative example 4) were prepared.

Example 4

Transformation of Pennate Diatoms

A pennate diatom *Phaeodactylum tricornutum* was transformed using the plasmid vectors of Example 2, Comparative example 1 and Comparative example 3.

Specifically, each plasmid vector was adhered to a tungsten particle M17 having an average particle diameter of 1.1 μm. Separately, pennate diatom *P. tricornutum* was spread on a solid-phase medium in an amount of $5 \times 10^7$ cells per one plate. The tungsten particle was hit into a cell at a He gas pressure of 1350 psi or 1100 psi by using a particle gun (manufactured by Bio-Rad, Biolistic PDS-1000/He Particle Delivery System). Then, the cell was cultured in a 1.0% agar f/2 medium containing 150 μg/mL Zeocin. The result is shown in Table 1.

Transformation of the colony of the cells grown in the medium containing antibiotic was confirmed by PCR. The colony of the grown cells was cultured in a 100 mL medium, and algal cells were collected, and then genomic DNA was extracted by a method similar to Example 1(1). PCR was carried out using the obtained genomic DNA as a template and the primer specific for the introduced antibiotic gene (ble). The condition of PCR reaction was basically similar to Example 1(2), and the cycle number was 40 and the annealing temperature was 60° C. An electrophoretic image analyzing the obtained amplified DNA is shown in FIG. 3.

Figure 3:
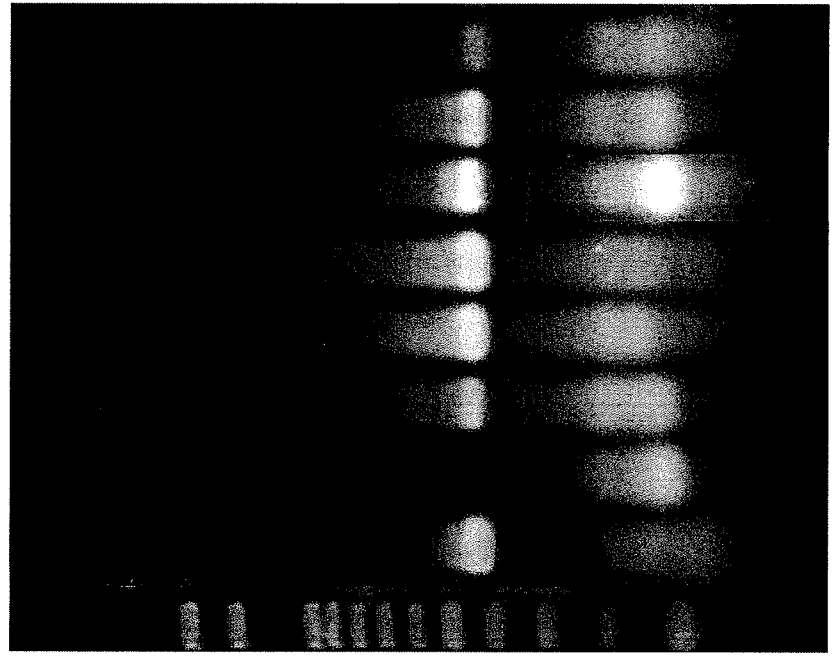
FIG. 3 is an electrophoresis photograph showing a result of an experiment for confirming presence of an introduced gene contained in an algal cell transformed by the present invention method.

In FIG. 3, "M" is a molecular weight marker, "1" is a lane of a plasmid vector into which an antibiotic gene (ble) was introduced, "2" is a lane of a wild type *P. tricornutum* strain, "3 to 5" are lanes of strains transformed with a plasmid vector containing a promoter derived from a cauliflower mosaic virus and an antibiotic gene (ble), and "6 to 8" are lanes of strains transformed with a plasmid vector containing a promoter according to the present invention and an antibiotic gene (ble).

Example 5

Transformation of Centric Diatoms

A centric diatom *Chaetoceros* sp. was transformed in a similar manner to Example 4 by using the plasmid vectors of Example 3, Comparative example 2 and Comparative example 4. In the present example, however, 500 μg/mL nourseothricin was added in a medium for culturing cells. The result is shown in Table 1.

TABLE 1

| Marine algae | Promoter | The number of transformed cells per $10^8$ of total cells (n = 2) |
|---|---|---|
| pennate diatom (*P. tricornutum*) | Endogenous promoter of Pennales diatoms | 69 |
| centric diatom (*Chaetoceros* sp.) | Endogenous promoter of Centrales diatoms | 1.0 |
| pennate diatom (*P. tricornutum*) centric diatom (*Chaetoceros* sp.) | Cauliflower mosaic virus promoter | 8.0 0 |
| pennate diatom (*P. tricornutum*) centric diatom (*Chaetoceros* sp.) | The invention promoter | 5.0 1.0 |

The transformation of the colony of the cells grown in the medium containing antibiotic was confirmed by PCR in a similar manner to Example 4. An electrophoretic image analyzing the obtained amplified DNA is shown in FIG. 4.

Figure 4:
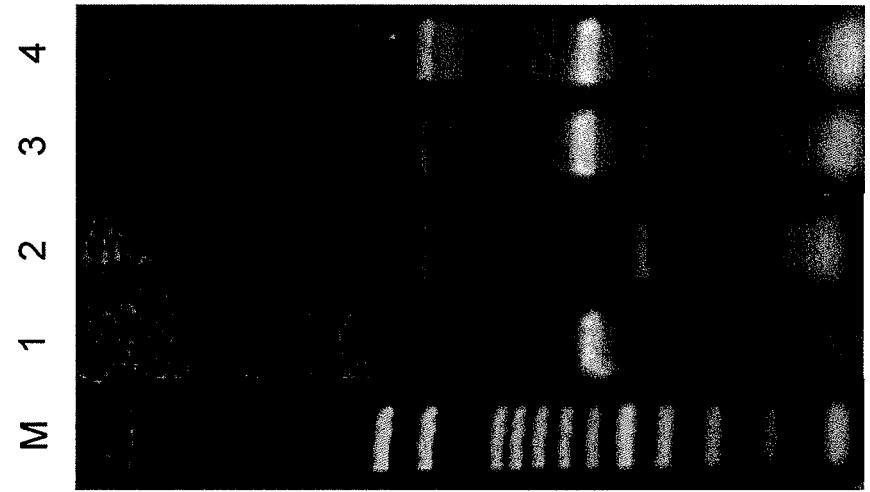
FIG. 4 is an electrophoresis photograph showing a result of an experiment for examining presence of an introduced gene contained in an algal cell transformed by the present invention method.

In FIG. 4, "M" is a molecular weight marker, "1" is a lane of a plasmid vector into which an antibiotic gene (nat) was introduced, "2" is a lane of a wild type *Chaetoceros* sp. strain, and "3 and 4" are lanes of strains transformed with a plasmid vector containing a promoter according to the present invention and an antibiotic gene (nat).

Example 6

Identification of a Core Element Region of a Promoter According to the Present Invention The DNA fragments each from the position +107 located upstream from a translation start point of the region encoding a replication-associated protein of a CdebDNA virus to the positions −72, −32, −2 and +34 were amplified in a similar manner to Example 1 except that primers of SEQ ID NOs: 6 to 9 were used in addition to the primer of SEQ ID NO: 3. The plasmids in which each of the entry clones, a nat and a fcp terminator were conjugated were prepared in a similar to Example 2 by using the entry clones, the entry clone containing a nourseothricin resistance gene (nat) prepared in Example 3 and the entry clone containing a fcp terminator derived from *Thalassiosira pseudonana*. The plasmids had a structure similar to the structure in FIG. 2. Transformation was carried out in a similar manner to Example 4 using a plasmid of Comparative example 2 and a plasmid to which a promoter was not connected (pNat/TpfcpTer) in addition to the plasmids. The result is shown in FIG. 5.

Figure 5:
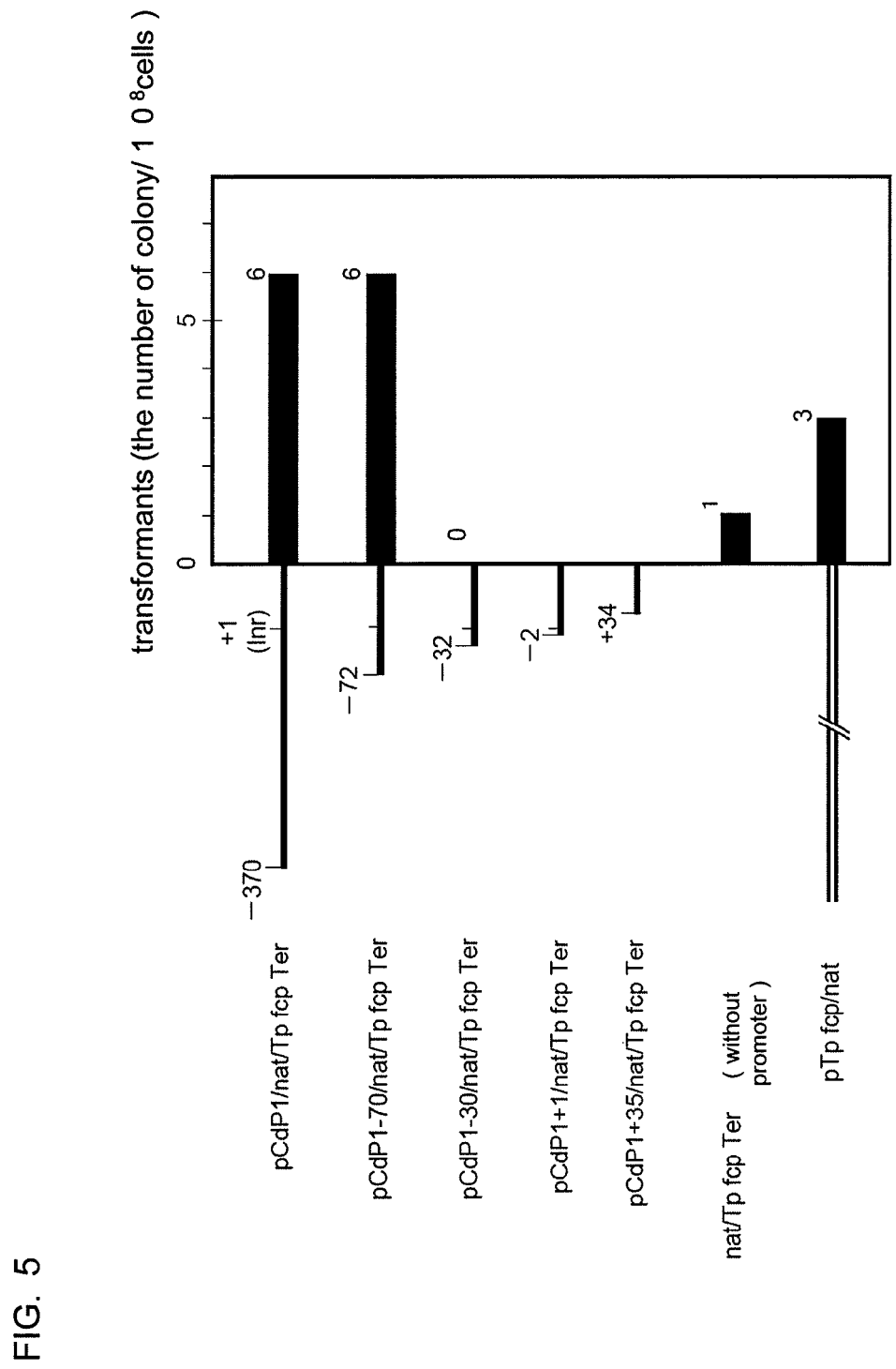
FIG. 5 is a graph showing a result of an experiment for identifying a core element of a promoter according to the present invention. This result reveals that a core element is included in a sequence of −72 to −33 in the region upstream from a gene encoding a replication-associated protein of a CdebDNA virus.

As shown in FIG. 5, transformation could be achieved when the nucleotide sequence from +107 to −370 (SEQ ID NO: 1) and the nucleotide sequence from +107 to −72 in the site upstream from the translation start point of the replication-associated protein gene were used as promoters, whereas transformation could not be achieved when the nucleotide sequence from +107 to −32 and the nucleotide sequence from −2 and +34 were used as promoters. From the result, it was concluded that a core element useful for transformation of algae highly possibly exists in the sequence from −72 to −33 (SEQ ID NO: 5) in the site upstream from the translation start point of the replication-associated protein gene. In addition, since there was a possibility that the transformation occurred by chance, a similar experiment was conducted using a plasmid not having a promoter. As a result, the transformation ratio was negligible. Further, a similar experiment was conducted using a promoter of centric diatom; as a result, the transformation ratio was clearly higher in the case of using the promoter of the present invention.

Example 7

Figure 6:
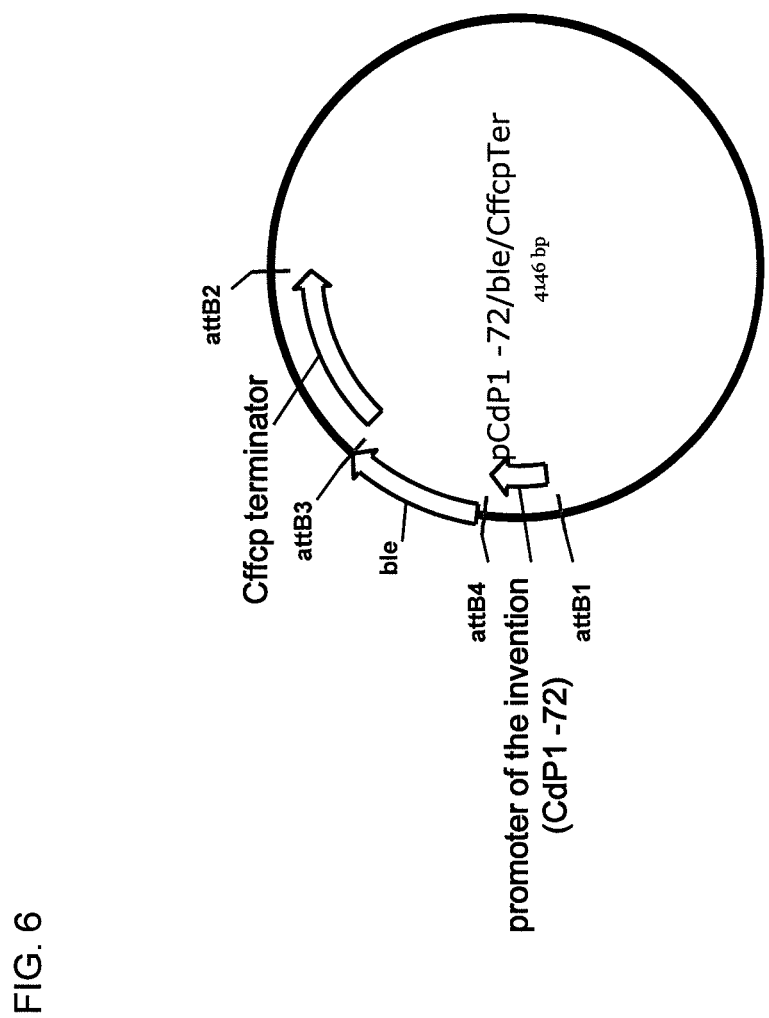
FIG. 6 is a view showing one example of a structure of a plasmid vector containing a promoter according to the present invention.
Figure 7:
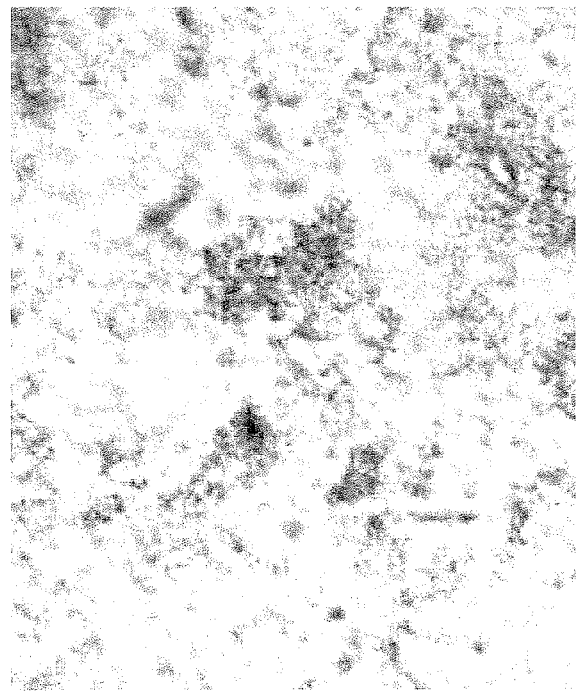
FIG. 7 is a photograph showing a result of a transformation experiment of C. fusiformis, which is a marine alga. (1) shows a result when the promoter of the present invention was used, and (2) shows a result when the promoter of the present invention was not used.
Figure 7:

Transformation of Various Marine Algae Using a Promoter of the Present Invention For confirming whether the promoter of the present invention is applicable to various species of diatoms, *C. fusiformis* which is a pennate diatom different from that in the above Example was transformed. A plasmid (FIG. 6) in which a Zeocin resistance gene (ble) and a terminator derived from a fcp gene of *C. fusiformis* were incorporated in addition to the bases from +107 to −72 in the site upstream from the translation start point of the region encoding a replication-associated protein of a CdebDNA virus was used. In a similar manner to Example 4, a plasmid was immobilized on a tungsten particle and transformation was carried out. As a control, a similar experiment was conducted using a plasmid (pBle/CffcpTer) that is identical except for not having the promoter. FIG. 7(1) shows a photograph of diatom when the plasmid having the promoter of the present invention was used, and FIG. 7(2) shows a photograph of diatom when the plasmid not having the promoter of the present invention was used.

As shown in FIG. 7(2), when the promoter of the present invention was not incorporated, the diatom died by the antibiotic possibly because transformation failed. On the contrary, when the promoter of the present invention was used, the diatom lived well as shown in FIG. 7(1), since the diatom was transformed and acquired antibiotic resistance. The result reveals that the promoter of the present invention enables transformation of diatoms other than the diatoms used in the above examples.

Discussion of Experimental Result (1) As to Transformability

As evidenced by the results of Examples 4 and 5, when an endogenous promoter of pennate diatom was used, a pennate diatom could be desirably transformed but a centric diatom could not be transformed at all. The same applied to a promoter of a cauliflower mosaic virus that is often used for transformation of plants, and also the promoter could transform a pennate diatom but could not transform a centric diatom at all.

On the contrary, when the promoter according to the present invention was used, as for pennate diatoms, two kinds of *P. tricornutum* and *C. fusiformis* could be transformed, and as for centric diatom, *Chaetoceros* sp. could be transformed. The three kinds of diatoms belong to classification groups that are systematically far from each other in the respective orders in a molecular phylogenetic tree of the entire diatoms. Therefore, it is supposed that the promoter of the present invention that is applicable to the species is applicable to a variety of diatoms.

Diatoms are broadly classified into pennate diatoms and centric diatoms, however, the specificity of a conventional promoter is high. On the other hand, the results show that the promoter according to the present invention can be widely used for efficient transformation of a variety of diatoms owing to the property of low specificity.

(2) As to a Nucleotide Sequence of a Promoter According to the Present Invention In general, there are a core promoter region to which a transcription binding factor for starting transcription binds and a gene transcription regulating region located upstream from the core promoter region in a promoter region of eukaryote. Also in a viral promoter, it is known that there are motif sequences often found in a core promoter region of eukaryote, such as a TATA box (5'-TATAWAW-3' (wherein W represents A or T)) and an initiator element (Inr). In light of the fact, a nucleotide sequence of the promoter of SEQ ID NO: 1 according to the present invention was analyzed by using PLACE Signal Scan Search (www.dna.affrc.go.jp/PLACE/) and compared.

As a result, in the promoter of the present invention, 5'-CAAT-3' (−97 to −94) which is CAAT box I, 5'-WGATAR-3' (−162 to −167) which is a GATA box, and 5'-CCA$_{+1}$TACC-3' (−2 to +5) which seems to be an initiator element were found in an upstream region, while a TATA box was not observed.

This initiator element resembles Inr sequences such as 5'-YYA$_{+1}$NWYY-3' of mammals (Javahery, R. et al., Molecular and Cellular Biology, 14, pp. 116-127 (1994)), 5'-YCA$_1$TTYY-3' of oomycetes (Mcleod, A et al., Eukaryotic Cell, 3, pp. 91-99 (2004)), 5'-TCA$_{+1}$KTY-3' of drosophila (wherein K represents G or T)(Purnell, B. A. et al., Genes & Development, 8, pp. 830-842 (1994)), 5'-TCA$_{+1}$YW-3' of trichomonas (Liston, D. R. et al., Molecular and Cellular Biology, 19, pp. 2380-2388 (1999)) and 5'-CCA$_{+1}$TTCC-3' in fcpA-1A which is a promoter of *C. fusiformis* (Poulsen, N. et al., FEBS Journal, 272, pp. 3413-3423 (2005)).

From the above information, it is also supposed that the initiator element found in the promoter of SEQ ID NO: 1 acted as a core element on both pennate diatoms and centric diatoms, and allowed transformation. However, it is impossible to transform centric diatoms by using fcpA-1A which is a promoter of *C. fusiformis* and resembles the initiator element.

Therefore, the high transformability exhibited by the polynucleotide (1) according to the present invention owes at least not to a TATA box or an initiator element but highly possibly to a completely unknown sequence acting as a core element.

(3) as to a Core Element of a Promoter According to the Present Invention

From the result of Example 6, the core element of the promoter according to the present invention is very likely to exist in the sequence between -72 and -33 (SEQ ID NO: 5) which locates in an upstream region of replication-associated protein gene of a CdebDNA virus. Since the sequence of SEQ ID NO: 5 is positioned about 30 to 70 bases upstream from the initiator element located in an upstream region of the replication-associated protein gene, it is difficult to consider that the initiator element functions as a core element. The sequence of SEQ ID NO: 5 was analyzed by PLACE Signal Scan Search (www.dna.affrc.go.jp/PLACE/), but no known motif sequence was found. Therefore, it is supposed that the core element of the promoter according to the present invention is a novel one that has not been conventionally known heretofore.

As shown in the above experimental results, the ability of transforming diatoms that belong to order of cetric as well as pennate diatoms is attributable to a novel sequence contained in the sequence of SEQ ID NO: 5 functioning as a core element.

INDUSTRIAL APPLICABILITY

By using a vector containing the promoter according to the present invention, a various kinds of algae can be transformed efficiently. Therefore, by using the present invention, it becomes possible to efficiently transform algae, of which transformation is difficult and for which the transformation technique has not been adequately examined although algae have excellent characteristics such as high photosynthetic capability and producibility of useful substance, and exist abundantly, in a wide range of diatoms

The invention claimed is:

1. A vector comprising a promoter and a heterologous gene encoding a protein, wherein the promoter comprises any one of the following polynucleotides (1) or (2):
   (1) a polynucleotide comprising SEQ ID NO: 1 or SEQ ID NO: 5; and
   (2) A polynucleotide which is a functional fragment of SEQ ID NO: 1, wherein the polynucleotide is capable of activating expression of a gene encoding an arbitrary protein in an algal cell.

2. The promoter according to claim 1, which comprises SEQ ID NO:5.

3. The promoter according to claim 1, which comprises SEQ ID NO:1.

4. A method for transforming an algal cell, comprising the steps of
   producing the vector according to claim 1; and
   introducing the vector into the algal cell.

* * * * *